United States Patent [19]

Hargrove et al.

[11] Patent Number: 4,819,860
[45] Date of Patent: Apr. 11, 1989

[54] WRIST-MOUNTED VITAL FUNCTIONS MONITOR AND EMERGENCY LOCATOR

[75] Inventors: James L. Hargrove, Vancouver, Canada; Lloyd D. Lillie, 35 - 1825 Atkinson Street, Penticton B.C., Canada, V2A 6Y5; Arthur T. Whittaker, 35 Westminster Avenue E., Penticton, B.C., Canada, V2A 1H7

[73] Assignees: Lloyd D. Lillie; Arthur T. Whittaker, both of British Columbia, Canada

[21] Appl. No.: 817,518

[22] Filed: Jan. 9, 1986

[51] Int. Cl.$^4$ ............................................. A61G 5/04
[52] U.S. Cl. ................................. 228/668; 128/736; 128/640; 128/903; 340/573
[58] Field of Search ............... 128/736, 903, 687, 668, 128/689–691, 670, 700, 706, 707, 666; 340/573; 364/417

[56] References Cited

U.S. PATENT DOCUMENTS

| | | | |
|---|---|---|---|
| 3,478,344 | 11/1969 | Schwitzgebel | 128/903 |
| 3,572,316 | 3/1971 | Vogelman et al. | 128/2.05 |
| 3,806,936 | 4/1974 | Koster | 343/113 |
| 3,858,574 | 1/1975 | Page | 128/2.05 |
| 3,902,478 | 9/1975 | Konopasek | 128/2.06 |
| 3,908,636 | 9/1975 | Page | 128/2.05 |
| 3,972,320 | 8/1976 | Kalman | 128/2.1 |
| 4,009,708 | 3/1977 | Fay, Jr. | 128/2.05 |
| 4,018,219 | 4/1977 | Hojaiban | 364/417 |
| 4,030,483 | 6/1977 | Stevens | 128/2.05 |
| 4,063,410 | 12/1977 | Welling | 128/903 |
| 4,100,536 | 7/1978 | Ball et al. | 340/207 R |
| 4,129,125 | 12/1978 | Lester et al. | 128/736 |
| 4,178,916 | 12/1979 | McNamara | 128/736 |
| 4,195,642 | 4/1980 | Price et al. | 128/689 |
| 4,202,350 | 5/1980 | Walton | 128/690 |
| 4,224,948 | 9/1980 | Cramer et al. | 128/690 |
| 4,230,127 | 10/1980 | Larson | 128/706 |
| 4,258,719 | 3/1981 | Lewyn | 128/690 |
| 4,280,506 | 7/1981 | Zurcher | 128/690 |
| 4,301,808 | 11/1981 | Taus | 128/687 |
| 4,305,401 | 12/1981 | Reissmueller et al. | 128/690 |
| 4,312,358 | 1/1982 | Barney | 128/736 |
| 4,394,777 | 7/1983 | Wren | 340/539 |
| 4,407,295 | 10/1983 | Steuer et al. | 128/670 |

FOREIGN PATENT DOCUMENTS

| | | |
|---|---|---|
| 2517453 | 10/1976 | Fed. Rep. of Germany . |
| 2922542 | 12/1980 | Fed. Rep. of Germany ...... 128/689 |
| 2386875 | 12/1978 | France ................ 128/903 |
| 2420333 | 11/1979 | France ................ 128/903 |
| 810730 | 3/1959 | United Kingdom ......... 128/903 |

OTHER PUBLICATIONS

"Telemetric Monitoring System for Medical Uses" by C. Tercier et al., Mitt. Agen (Switzerland) #15, Aug. 1973, pp. 5–13.
"A Telemetry System for Studying Elk Behavior in the Rocky Mountains" by Weeks et al Proc. of the 9th Annual Rocky Mountain Bioeng. Symp. and the 10th Int. ISA Biomed. Sci. Inst. Symp., vol. 9, Omaha Neb., 1-3 May 1972.

Primary Examiner—Lee S. Cohen
Assistant Examiner—David Shay
Attorney, Agent, or Firm—Spensley Horn Jubas & Lubitz

[57] ABSTRACT

A wrist-mounted pulse rate and body temperature monitor has means for storing upper and lower emergency pulse rates and body temperatures by means of which an emergency medical situation is defined. When the monitor detects an emergency medical situation, an emergency signal is generated on standard emergency locator frequencies to alert search and rescue services. Means for automatically setting the upper and lower safe thresholds is provided. The device is particularly suited for use by individuals in remote areas where either the health of the individual or the environment create a higher risk to the survival of the individual.

9 Claims, 2 Drawing Sheets

WRIST-MOUNTED VITAL FUNCTIONS MONITOR AND EMERGENCY LOCATOR

BACKGROUND OF THE INVENTION

1. Field of the Invention

The present invention relates to emergency signal transmitters for the purpose of summoning medical aid in the event of a medical emergency, such as in remote areas. In particular, the present invention relates to a wristmounted vital functions monitor for automatically detecting a medical emergency situation and generating the required emergency radio signal.

2. Description of the Prior Art

Emergency locator radio transmitters are commonly used in airplanes to generate a radio signal to assist search and rescue teams in locating an airplane in the event of a crash. Similar emergency locators have been developed for personal use, which locators can be actuated by the individual, such as a hunter or fisherman, in the event that the individual becomes lost. Examples of such personal locators are disclosed in U.S. Pat. No. 3,806,936 issued Apr. 23, 1974 to Aero Electronics Development Co. and in U.S. Pat. No. 4,121,160 issued Oct. 17, 1978 to Cataldo. Such emergency locators require, however, that the individual be sufficiently healthy and lucid to appreciate his predicament and activate the device.

Systems are also known for the remote monitoring of the vital functions of hospital patients whereby such vital functions as pulse rate and body temperature are remotely monitored on the patient and an emergency signal is transmitted to a central monitoring station by radio transmitter if the pulse rate or temperature suggests an emergency situation. Such systems are disclosed in U.S. Pat. No. 3,972,320 issued Aug. 3, 1976 to Kalman and U.S. Pat. No. 3,902,478 issued Sept. 2, 1975 to Konopasek et al. Such systems are not well adapted for use as emergency locators for sportsmen and the like, as they require setting of the pulse rate parameters by a physician, require connection of electrodes to the patient's skin to monitor the heart (as in Kalman) and are not suitably self sufficient in terms of battery power to be reliable in remote locations.

SUMMARY OF THE INVENTION

The present invention provides a vital functions monitoring device and emergency locator which is well-suited for use by individuals such as sportsmen in remote locations. The present invention is worn easily on the user's wrist without the necessity of special installation, is sufficiently power-efficient for reliable use as an emergency locator in remote locations, and has means for easily setting the safe pulse rate and body temperature limits.

The present invention provides a portable vital functions monitoring device and emergency signal generator which comprises clock means, sensing means for measuring the pulse rate of an individual, means for measuring the body temperature of an individual, means for comparing the current pulse rate and body temperature of the individual to pre-set limits, and means for generating an emergency radio signal if the measured pulse rate and body temperature indicate an emergency medical situation. According to one aspect of the invention, the device is secured to the wrist of the user by a wrist strap. According to a further aspect of the invention, the invention further comprises means for establishing the predetermined limits by recording the maximum and minimum pulse rates and temperatures of the individual over a given period of time.

BRIEF DESCRIPTION OF THE DRAWINGS

In drawings which illustrate an embodiment of the invention.

DETAILED DESCRIPTION OF THE PREFERRED EMBODIMENT

Figure 1:
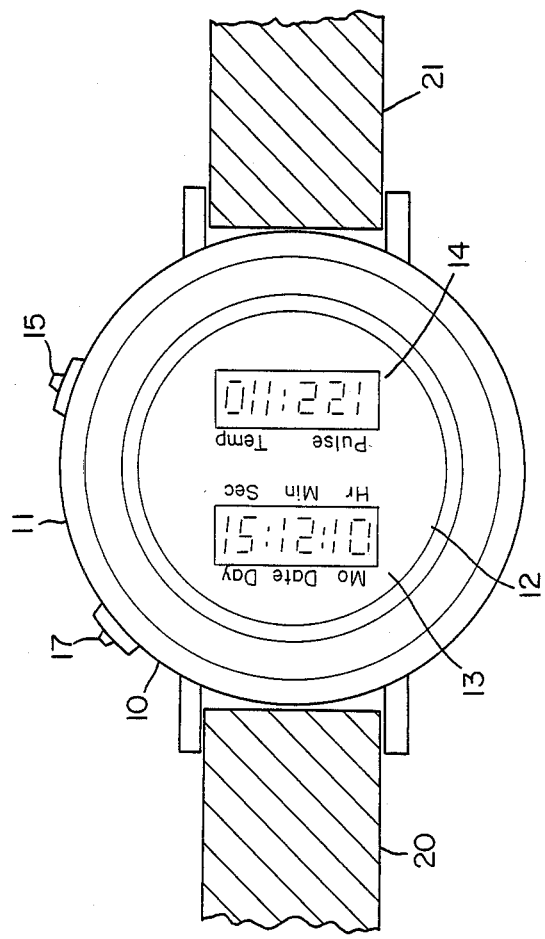
FIG. 1 is a front face view of an embodiment of the invention.

Referring to FIG. 1, the wrist-mounted monitoring device of the invention is shown generally as 10. The device has a casing 11 with a front face region 12 and a pair of windows 13 and 14 having means for digital display such as light emitting diodes or liquid crystal. Depending on the function selected, the windows display time, date, alarm settings, pulse rate and body temperature readings. The device is provided with two control buttons 15 and 17, one of which selects the function and the other of which controls the function selected. The device is provided with straps 20 and 21 to secure the device on the user's wrist and which may function as antennae for the transmitter.

Figure 2:
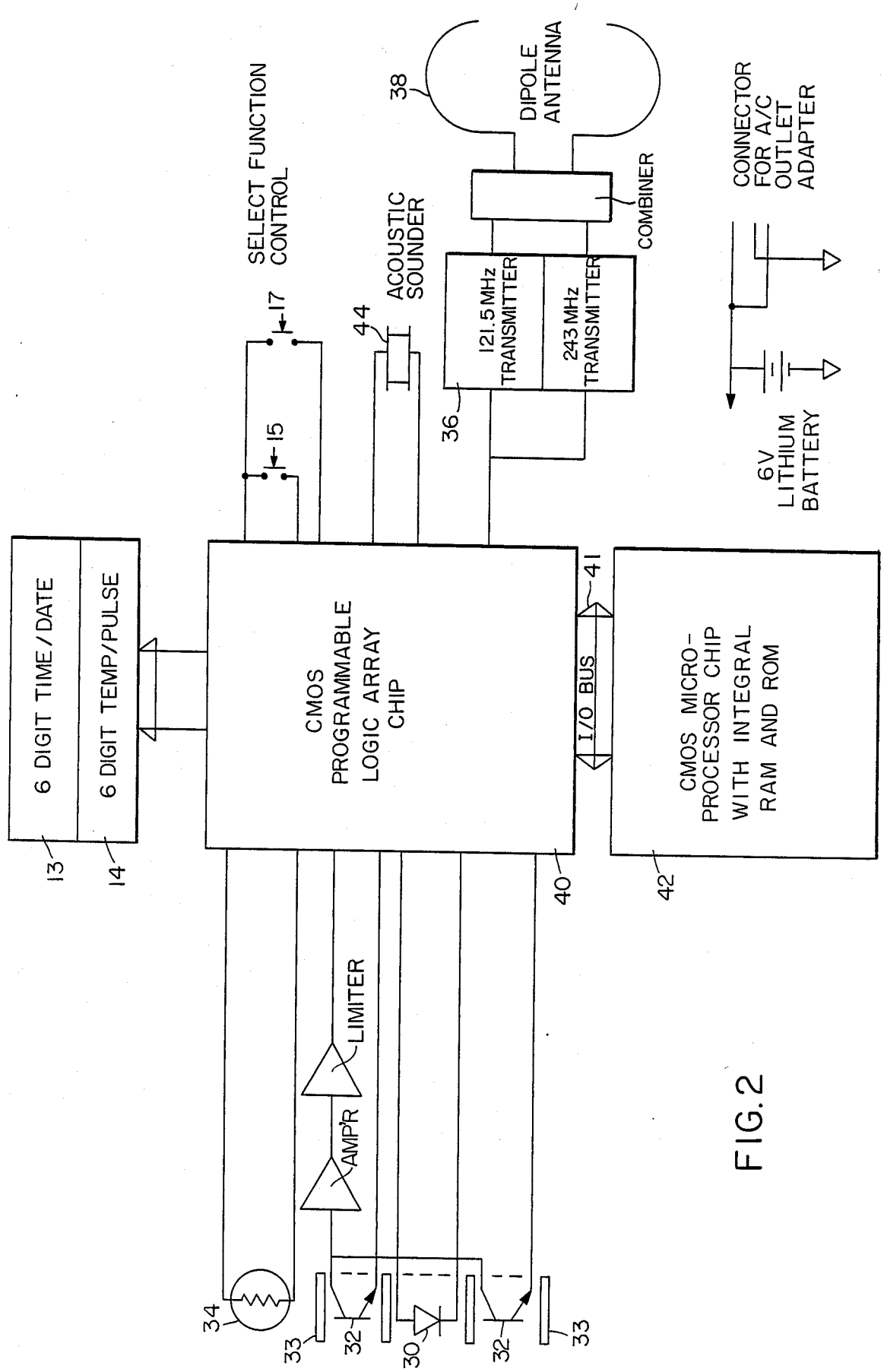
FIG. 2 is a schematic diagram illustrating the circuit components of the invention.

The underside of the device 10 (not shown) which bears against the user's skin is provided with the pulse and temperature sensors. The preferred pulse sensor is of the type described in U.S. Pat. No. 4,224,948 issued Sept. 30, 1980 to Cramer. An infra-red light source 30 in FIG. 2, preferably a light-emitting diode, bears against the user's skin and the light is detected by one or more infra-red photo-detectors 32 also on the underside of the device bearing against the skin. The photo-detectors, which may be photo-transistors, are shielded from direct transmission from the light emitting diode, to detect only the indirect infra-red radiation diffused through the skin and capillaries beneath the skin. This may be done, as in the Cramer wrist-borne pulse meter/chronometer, by a coaxial arrangement of the central light-emitting diode, a circular shielding boss 33, and a circular detector array. As the variation in the flow of blood through the capillaries causes a variation in infrared transmissivity, the sensor output will reflect the variation in blood flow and thus the pulse rate. In order to save power, the infra-red signal will be pulsed at the shortest possible duty cycle which allows satisfactory detection of the radiation and at a high enough rate that accurate detection of the pulse rate frequency is possible. Approximately ten pulses of the light-emitting diode per heart pulse, or about twenty-five per second, are required as a minimum for accurate estimation of the pulse rate. The signal from the photo-detectors is amplified, converted to a square wave and is passed to the central processor.

The temperature sensor 34 is also located on the underside of the device and consists of a thermistor, such as a National Semiconductor LM 134 or 135 or similar thermistor, which acts as a temperature-to-frequency converter. The output of the sensor is also inputted to the device's central processor.

The device incorporates a miniature two-frequency transmitter 36 with its short dipole antenna 38 embedded in the wrist strap of the device. The preferred form of the invention transmits on the two standard emergency locator frequencies 121.5 and 243 Megahertz. If further power conservation is required and to minimize the size of the device, transmission can be limited to the 243 Megahertz band. The transmitter is pulse code modulated with a six-digit Morse code identifier in order to identify the individual user. The transmitter transmits periodically, for example, once every ten or twenty seconds, once activated, in order to minimize power consumption and extend battery life. Preferably a six-volt lithium battery is used to maximize operating life, and the unit may be adapted to recharge the battery from an AC outlet.

A programmable logic array 40 is used to process signals from the sensors, to drive the liquid crystal display of time and date 13 and temperature and instantaneous or average pulse rate, and to activate the emergency signal transmitter and the acoustical alarm 44. Suitable programmable logic arrays are manufactured by Texas Instruments and Advanced Micro Devices. The programmable logic array interfaces through input/output bus 41 with a complementary metal oxide silicon (CMOS) microprocessor 42 with integral random acess memory and read only memory. The microprocessor is clocked by a 32.768 kilohertz crystal and is programmed in the read only memory to keep time, measure pulse rate and temperature, drive the liquid crystal display, determine whether pulse rate and temperature have moved beyond the predetermined thresholds, provide on/off signals for the acoustical alarm and the emergency locator transmitter, and to perform the other control functions. A suitable CMOS micro processor is the Motorola MC 146805 F2 or G2.

Two control buttons 15 and 17 are utilized, one selecting the funcion to be performed and the other controlling the selected function. By this arrangement, the possibility of accidentally activating the emergency locator transmitter is reduced. The controls are auto-stepping if held on for longer than one second and step at a rate which permits easy selection of the desired value. The following table sets out the preferred functions and controls.

| ITEM NO. | Function | Action No. | Control |
|---|---|---|---|
| 1 | Time/Date | 1 | Time/Date |
| 2 | Temp/Pluse | 1 | Temp/Pulse |
| 3 | Time Alarm | 1 | On/Off |
| 4 | Set Month | As nec. | Increment Month |
| 5 | Set Date | As nec. | Increment Date |
| 6 | Set Day | As nec. | Increment Day |
| 7 | Set Alarm Hour | As nec. | Increment Alarm Hour (1-12, AM & PM) |
| 8 | Set Alarm Min. | As nec. | Increment Min. (00-59) |
| 9 | Set Hour | As nec. | Increment Hour (1-12, AM & PM) |
| 10 | Set Minute | As nec. | Increment Minute (00-59) |
| 11 | Set Seconds | 1 | Zero Seconds |
| 12 | Set Low Temp. | As nec. | Increment Low Limit (0-100, °F. or °C.) |
| 13 | Set High Temp. | As nec. | Increment High Limit (0-100, °F. or °C.) |
| 14 | Set Low Pulse | As nec. | Increment Low Limit (30-200 PPM) |
| 15 | Set High Pulse | As nec. | Increment High Limit (30-200 PPM) |
| 16 | Auto Hi/Lo Pulse/Temp. | 1 | On/Off Measures (Upper and Lower Limits over 24 hr. period) |
| 17 | Sel Temp Alarm | 1 | On/Off |
| 18 | Sel Pulse Alarm | 1 | On/Off |
| 19 | Sel ELT* | 1 | On/Off |

*Emergency locator transmitter

For example, when the function number 1 is selected the time is displayed in window 13 and the date is displayed when the control button is pushed on. The time, pulse and temperature alarms all may be manually set and will activate both a flashing display and the acoustic alarm. Functions are provided for deactivating the alarm.

Provision is made for automatically setting the pulse and temperature levels at which the emergency locator transmitter is activated. By activating this function (No. 16), the pulse rate and temperature are monitored over a 24-hour period and the highest and lowest readings recorded over the period are stored. (Readings are averaged over a minimum interval prior to comparison to avoid anomalous instantaneous readings.) The user would arrange a period of strenuous activity, such as a treadmill test, during the recording period to determine the maximum safe pulse rate, as well as a rest or sleep period for setting the lower levels. The upper and lower limits would be entered in the appropriate memory register. The device would then be programmed to generate the emergency locator signal if pulse or temperature readings bore a pre-determined relationship to the maximum and minimum levels stored. to avoid false alarms due to anomalous instantaneous readings, again either the readings are averaged over an interval before comparison, or a minimum successive number of high or low readings is required to activate the alarm.

In operation, the user would select the auto high/low pulse/temperature function to set his high/low pulse and temperature thresholds for the device. If the individual then encountered a medical risk situation, such as hypothermia or heart failure in a remote location, the emergency locator transmitter would be activated and search and rescue authorities would be notified so that a rescue could be performed.

As will be apparent to those skilled in the art in light of the foregoing disclosure, many alterations and modifications are possible in the practice of the invention without departing from the spirit or scope thereof, which is defined by the appended claims.

The embodiments of the invention in which an exclusive property or privilege is claimed are defined as follows:

1. A portable vital functions monitoring device and emergency signal generator comprising:
   (a) a housing adapted for mounting against the skin of an individual
   (b) means for securing said housing against the skin of said individual;
   (c) pulse rate sensing means mounted on said housing for contact with said skin and for sensing the pulse rate of an individual and for producing a pulse rate output signal representative thereof;
   (d) computing means responsive to said pulse rate output signal for computing an instantaneous pulse rate of said individual and for producing a signal representative thereof;
   (e) clock means for measuring a period of time;
   (f) information storage means;

(g) means for monitoring said instantaneous pulse rate over a period of time sufficient to include periods of rest and periods of extreme physical activity of said individual and for storing in said information storage means the highest and lowest values of said instantaneous pulse rate monitored over said period of time;

(h) comparison means for comparing said instantaneous pulse rate value to said stored values in said information storage means; and (i) means for producing an emergency radio alarm signal in the event that said comparison indicates that said instantaneous pulse rate value is above the highest stored value in said information storage means or below said lowest stored value in said information storage means.

2. A portable vital functions monitoring device and emergency signal generator comprising:

(a) a housing adapted for mounting against the skin of an individual;

(b) means for securing said housing against the skin of said individual;

(c) pulse rate sensing means mounted on said housing for contact with said skin and for sensing the pulse rate of an individual and for producing a pulse rate output signal representative thereof.

(d) temperature sensing means mounted on said housing for contact with said skin and for sensing the body temperature of said individual and for producing a temperature output signal representative thereof;

(e) computing means responsive to said pulse rate output signal for computing an instantaneous pulse rate of said individual and for producing a signal representative thereof;

(f) clock means for measuring a period of time;

(g) information storage means;

(h) means for monitoring said instantaneous pulse rate and said temperature output signal over a period of time sufficient to include periods of rest and of extreme physical activity of said individual and for storing in said information storage means the highest and lowest values of said instantaneous pulse rate and said temperature output monitored over said period of time;

(i) comparison means for comparing said instantaneous pulse rate and said temperature output signal to said values stored in said information storage means; and (j) means for producing an emergency radio alarm signal in the event that said comparison indicates that the pulse rate or body temperature of said individual are outside the extreme limits stored in said information storage means.

3. The portable vital functions monitoring device of claim 1 wherein said emergency radio signal is transmitted on a standard emergency locator frequency.

4. The portable vital functions monitoring device of claim 3 wherein said emergency radio signal is pulse code modulated with a unique identity code.

5. The portable vital functions monitoring device of claim 2 wherein said emergency radio signal is transmitted on a standard emergency locator frequency.

6. The portable vital functions monitoring device of claim 5 wherein said emergency radio signal is pulse code modulated with a unique identity code.

7. The portable vital functions monitoring device of claim 1 wherein said housing is adapted to be secured to the wrist of said individual and wherein said means for securing said housing against the skin of said individual comprises a wrist strap.

8. The portable vital functions monitoring device of claim 7 wherein said wrist strap further comprises antenna means for transmitting a signal associated with said means for producing an emergency radio alarm signal.

9. A method of monitoring the vital functions of an individual in remote locations comprising:

(a) sampling the instantaneous pulse rate and body temperatures of said individual over a period of time sufficient to include periods of rest and extreme physical activity;

(b) storing the highest and lowest pulse rates and body temperatures recorded during said period or time;

(c) monitoring the instantaneous pulse rate and body temperature of said individual while in said remote location;

(d) comparing said monitored values of said instantaneous pulse rate and body temperature to said stored values; and (e) sending an emergency radio signal if said monitored values for said instanteous pulse rate or body temperature are above said stored highest values or below said stored lowest values.

* * * * *